(12) United States Patent
Wentling

(10) Patent No.: US 7,988,128 B2
(45) Date of Patent: Aug. 2, 2011

(54) SEALING LUER

(75) Inventor: Angela Wentling, Sassamansville, PA (US)

(73) Assignee: Medical Components, Inc., Harleysville, PA (US)

( * ) Notice: Subject to any disclaimer, the term of this patent is extended or adjusted under 35 U.S.C. 154(b) by 411 days.

(21) Appl. No.: 10/857,427

(22) Filed: May 28, 2004

(65) Prior Publication Data

US 2004/0249349 A1    Dec. 9, 2004

Related U.S. Application Data

(60) Provisional application No. 60/475,735, filed on Jun. 4, 2003.

(51) Int. Cl.
*F16K 51/00* (2006.01)
(52) U.S. Cl. ........... 251/286; 251/367; 604/32; 604/248
(58) Field of Classification Search .......... 251/208, 251/209, 309, 310, 367, 289; 604/30, 32, 604/246, 248, 167.05, 167.08; 137/556.6, 137/556.3; 285/286–288
See application file for complete search history.

(56) References Cited

U.S. PATENT DOCUMENTS

| | | | | |
|---|---|---|---|---|
| 983,643 | A | * | 2/1911 | Pierce ........................... 303/81 |
| 2,994,341 | A | * | 8/1961 | Leopold, Jr. et al. ......... 251/288 |
| 3,168,280 | A | * | 2/1965 | Mueller ........................ 251/217 |
| 3,185,179 | A |   | 5/1965 | Harautuneian |
| 3,532,116 | A | * | 10/1970 | Huie et. al. .................. 137/550 |
| 3,983,203 | A |   | 9/1976 | Corbett |
| 4,051,866 | A | * | 10/1977 | Bake et al. .................... 251/288 |
| 4,111,395 | A | * | 9/1978 | Sheppard ....................... 251/367 |
| 4,265,427 | A | * | 5/1981 | Vinciguerra ................... 251/367 |
| 4,294,250 | A |   | 10/1981 | Dennehey |
| 4,689,047 | A |   | 8/1987 | Bauer |
| 4,696,323 | A | * | 9/1987 | Iff ................................. 251/367 |
| 4,744,390 | A | * | 5/1988 | Henry ........................... 251/288 |
| 4,846,223 | A | * | 7/1989 | Humbert, Jr. ............. 137/625.19 |
| 5,019,054 | A | * | 5/1991 | Clement et al. ............... 604/248 |
| 5,029,811 | A | * | 7/1991 | Yamamoto et al. ........... 251/367 |
| 5,074,334 | A |   | 12/1991 | Onodera |
| 5,149,054 | A | * | 9/1992 | Passerell et al. .............. 251/309 |
| 5,156,186 | A | * | 10/1992 | Manska ........................ 137/556 |
| 5,184,742 | A |   | 2/1993 | DeCaprio et al. |
| 5,234,193 | A | * | 8/1993 | Neal et al. ..................... 251/175 |
| 5,370,624 | A |   | 12/1994 | Edwards et al. |
| 5,395,342 | A | * | 3/1995 | Yoon ........................ 604/167.03 |
| 5,395,348 | A | * | 3/1995 | Ryan ............................ 604/247 |
| 5,474,526 | A |   | 12/1995 | Danielson et al. |
| 5,522,430 | A | * | 6/1996 | Mittersteiner Urzua . 137/625.47 |
| 5,535,785 | A |   | 7/1996 | Werge et al. |

(Continued)

*Primary Examiner* — John K Fristoe, Jr.
*Assistant Examiner* — Andrew J Rost
(74) *Attorney, Agent, or Firm* — Anton P. Ness; Fox Rothschild, LLP

(57) ABSTRACT

A connector (100) for a medical device including a body (110) having a proximal end (114), a distal end (112), and a passage (116) extending therethrough between the proximal end and the distal end that fluidly connects the proximal end and the distal end. The proximal end (114) includes a connecting portion (119) for releasably connecting the connector to an external device. The distal end (112) is fluidly connected to a conduit. A cylinder (124) is rotatably disposed in the passage (116) between first position and a second position, wherein the cylinder includes an opening (128) extending generally diametrically therethrough. One or both ends (130, 132;230,232) of the cylinder provide manually- or tool-engageable sections (136;236) to enable rotation of the cylinder between open and closed positions, allowing and preventing fluid flow through the connector (100), respectively.

10 Claims, 4 Drawing Sheets

U.S. PATENT DOCUMENTS

| | | | |
|---|---|---|---|
| 5,620,427 A | 4/1997 | Werschmidt et al. | |
| 5,935,110 A * | 8/1999 | Brimhall | 604/167.06 |
| 5,954,657 A | 9/1999 | Rados | |
| 6,152,173 A * | 11/2000 | Makowan | 137/556.3 |
| 6,269,704 B1 | 8/2001 | Ziv et al. | |
| 6,880,808 B2 * | 4/2005 | McPeak et al. | 251/309 |

* cited by examiner

US 7,988,128 B2

SEALING LUER

CROSS REFERENCE TO RELATED APPLICATION

The present application claims priority from U.S. Provisional Patent Application Ser. No. 60/475,735, filed Jun. 4, 2003.

FIELD OF THE INVENTION

The present invention relates to a connecting luer for a medical device, such as a catheter, that incorporates a sealing device therein.

BACKGROUND OF THE INVENTION

Catheters may be located in various venous locations and cavities throughout the body of a patient for introduction of fluids to a body or removal of fluids from the body. Such catheterization may be performed by using a single catheter having multiple lumens. A typical example of a multiple lumen catheter is a dual lumen catheter assembly in which one lumen introduces fluid and the other lumen removes fluid. An example of such a dual lumen catheter assembly is the SPLIT-CATH® catheter. Alternatively, catheterization may be performed by using multiple single-lumen catheters, such as TESIO® catheters.

Generally, to insert any catheter into a blood vessel, the vessel is identified by aspiration with a long hollow needle in accordance with the well known Seldinger technique. When blood enters a syringe attached to the needle, indicating that the vessel has been found, a thin guidewire is then introduced, typically through a syringe needle or other introducer device into the interior of the vessel. The introducer device is then removed, leaving the guidewire within the vessel. The guidewire projects beyond the surface of the skin. At this point, several options are available to a physician for catheter placement. The simplest is to pass a catheter into the vessel directly over the guidewire. The guidewire is then removed, leaving the catheter in position within the vessel. However, this technique is only possible in cases where the catheter (for example, a small diameter dual lumen catheter) is of a relatively small diameter, made of a stiff material, and not significantly larger than the guidewire. If the catheter to be inserted is significantly larger than the guidewire, a dilator device containing a sheath is passed over the guidewire to enlarge the opening in the vessel. The dilator is then removed along with the guidewire, leaving the sheath in place, and the catheter is then passed through the sheath into the vessel. The guidewire is then removed, leaving the catheter in position within the vessel.

Each catheter lumen is typically connected to a distal end of an extension tube via a hub. The extension tube has a standard connector at its proximal end for connection to a medical device, such as a hemodialysis machine. Such connectors are commonly referred to as "luers". A luer includes standard male threads for connection of a cap to the luer when the luer is disengaged from the hemodialysis machine to prevent blood from flowing out of the catheter. As a backup to the cap, a clamp, such as a Roberts clamp, is typically disposed over the extension tube. The clamp restricts fluid flow through the extension tube by compressing and closing the extension tube between a pair of clamp jaws. For long term catheterization, the clamp must be opened and closed numerous times, which may lead to a failure of the extension tube and blood loss from the catheter. It would be beneficial to provide an alternate method of providing a backup for the cap to secure the catheter between dialysis treatments.

BRIEF SUMMARY OF THE INVENTION

Briefly, the present invention provides a connector for a medical device. The connector comprises a body having a proximal end, a distal end, and a passage extending therethrough between the proximal end and the distal end that fluidly connects the proximal end and the distal end. The proximal end includes a fitting for releasably connecting the connector to an external device and the distal end is fluidly connected to a conduit. A sealing member is disposed within the passage to selectively restrict fluid flow between the proximal end and the distal end.

Additionally, the present invention provides a connector for a medical device. The connector comprises a body having a proximal end, a distal end, and a passage extending therethrough between the proximal end and the distal end that fluidly connects the proximal end and the distal end. The proximal end includes a fitting for releasably connecting the connector to an external device and the distal end is fluidly connected to a conduit. A cylinder is rotatably disposed in the passage between first position and a second position, wherein the cylinder includes an opening extending generally diametrically therethrough.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain the features of the invention. In the drawings.

DETAILED DESCRIPTION OF THE INVENTION

Figure 1:
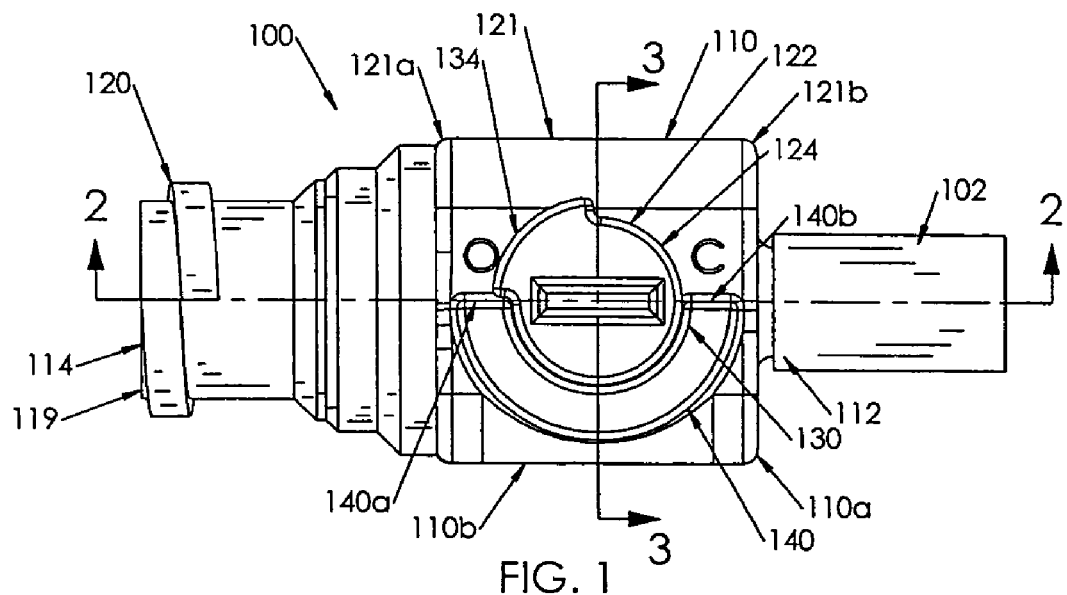
FIG. 1 is a side elevational view of a sealing luer according to a first embodiment of the present invention, with a sealing valve in the open position.

In the drawings, like numerals indicate like elements throughout. Certain terminology is used herein for convenience only and is not to be taken as a limitation on the present invention. The words "proximal" and "distal" refer to directions closer to and away from, respectively, the catheter extension connected to the locking luer according to the present invention. The terminology includes the words above specifically mentioned, derivatives thereof, and words of similar import. The following describes preferred embodiments of the invention. However, it should be understood based on this disclosure, that the invention is not limited by the preferred embodiments described herein.

Referring now to FIGS. 1-4, a connector or sealing luer 100 according to a first embodiment of the present invention is shown. The sealing luer 100 may be used to restrict fluid flow through a fluid system, such as a hemodialysis catheter, or any other medical device through which fluid flows. The sealing luer 100 connects a fluid conduit, such as a catheter 102, to a medical device, such as a hemodialysis machine (not shown). Alternatively, when the catheter 102 is not connected to the medical device, a cap (not shown) may be releasably disposed over a proximal end 114 of the sealing luer 100 to further restrict fluid flow through the fluid system.

The sealing luer 100 includes a body 110 having a distal end 112 and the proximal end 114. A longitudinal passage 116 extends through the body 110 between the distal end 112 and the proximal end 114. The distal end 112 is preferably fixedly connected to the catheter 102. The distal end 112 may be connected to the catheter 102 by an interference fit or an adhesive. Alternatively, the distal end 112 may include a barbed fitting (not shown), or other suitable connection, as will be recognized by those skilled in the art. The proximal end 114 may include a fitting, such as a luer fitting 119 shown in FIG. 1. Alternatively, the fitting may be a slip lock fitting (not shown), or some other suitable fitting. The luer fitting 119 releasably connects the sealing luer 100 to an external device, such as a hemodialysis machine (not shown). The luer fitting 119 includes a threaded male connection 120 for releasably retaining a cap (not shown) thereon when the catheter 102 and the luer 100 are not in use.

Referring to FIGS. 1-4, the body 110 further includes a valve body 121 disposed along the longitudinal passage 116 between the distal end 112 and the proximal end 114. The valve body 121 includes a proximal body end 121a and a distal body end 121b. Preferably, the valve body 121 is constructed from polyvinylchloride (PVC) or some other suitable, biocompatible material, as will be recognized by those skilled in the art. The valve body 121 includes a valve passage 125 that extends generally perpendicular to the longitudinal passage 116. A valve 122 is rotatably disposed in the valve passage 125. Preferably, the valve 122 is constructed from nylon or some other suitable, biocompatible material, as will be recognized by those skilled in the art. The valve 122 includes a cylinder 124 having a longitudinal axis 126 that extends generally perpendicularly to the longitudinal passage 116, such that the cylinder 124 is rotatable about the longitudinal axis 126. An enlarged view of the cylinder 124 is shown in FIG. 5.

Figure 2:
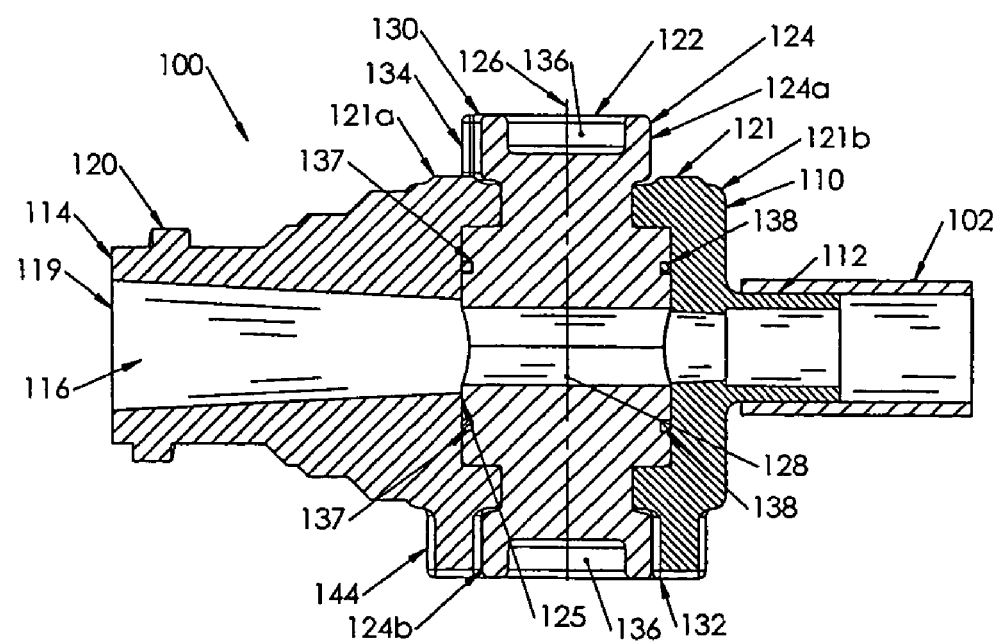
FIG. 2 is a longitudinal sectional view of the sealing luer according to the first embodiment of the present invention, taken along lines 2-2 of FIG. 1.
Figure 3:
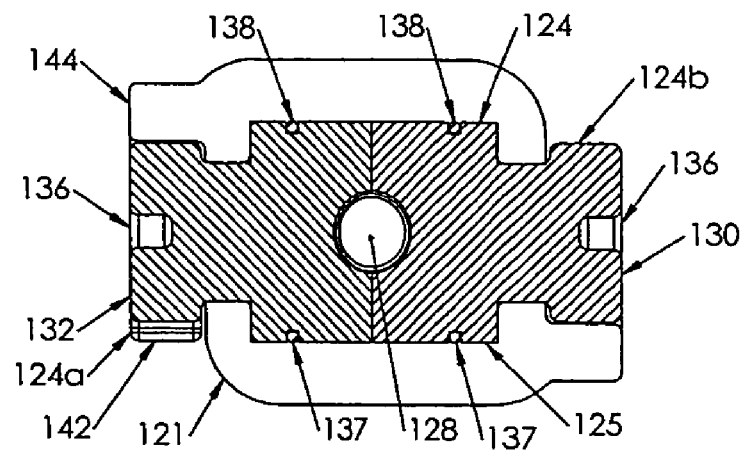
FIG. 3 is a lateral sectional view of the sealing luer according to the first embodiment of the present invention, taken along lines 3-3 of FIG. 1.
Figure 4:
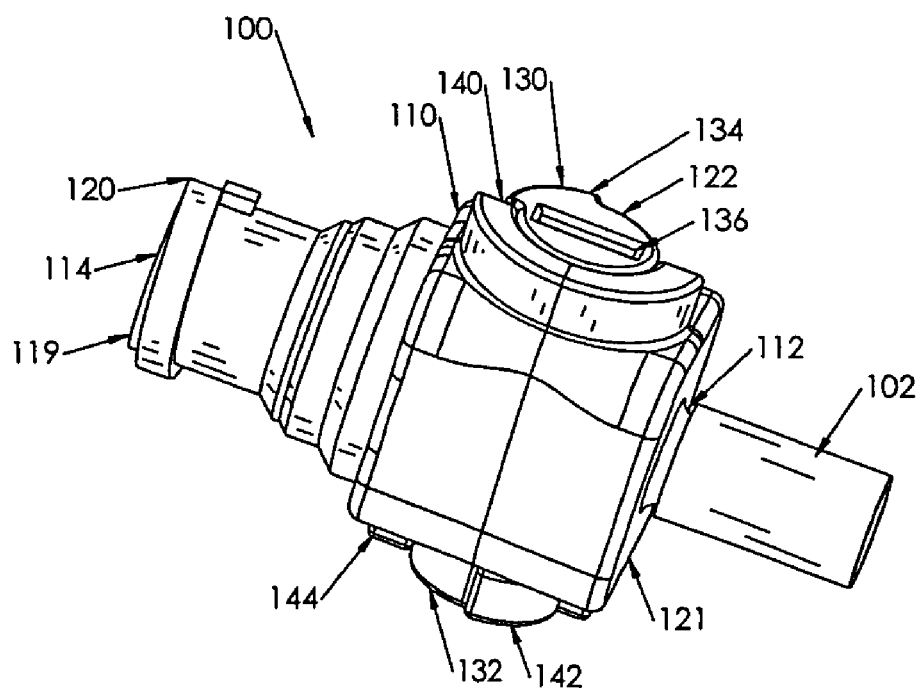
FIG. 4 is a perspective view of the sealing luer according to the first embodiment of the present invention.
Figure 5:
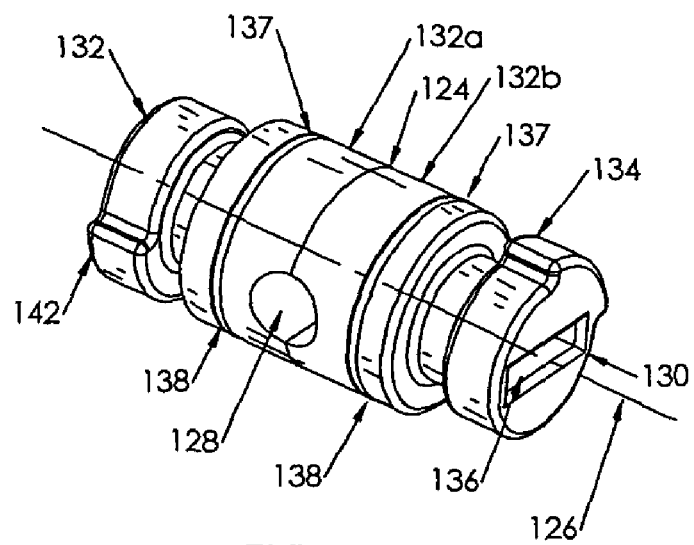
FIG. 5 is an enlarged view, in perspective, of a cylinder used in the sealing luer according to the first embodiment of the present invention.

Referring to FIGS. 2 and 5, the cylinder 124 includes an opening 128 that extends generally diametrically through the cylinder 124, generally perpendicular to the longitudinal axis 126 of the cylinder 124. The opening 128 is preferably cylindrical in shape and is approximately the same diameter as the smallest diameter of the longitudinal passage 116 so that, when the opening 128 is aligned with the longitudinal passage 116, as shown in FIG. 2, fluid communication within the passage 116 between the distal end 112 and the proximal end 114 and through the opening 128 is minimally restricted. The cylinder 124 is rotatably disposed within the body 121 so that, when the opening 128 is generally perpendicular to the longitudinal passage 116, fluid communication within the passage 116 between the distal end 112 and the proximal end 114 and through the opening 128 is restricted.

Referring now to FIGS. 1-5, the cylinder 124 includes a first end portion 130 that extends in a first plane generally perpendicular to the longitudinal axis 126 of the cylinder 124 and, optionally, a second end portion 132 that extends in a second plane generally perpendicular to the longitudinal axis 126 of the cylinder 124. The first end portion 130 includes thereon an actuating section such as a generally arcuate first tab 134 extending therefrom. As shown in FIG. 1, the first tab 134 defines an arc that extends preferably approximately 90 degrees around the outer perimeter of the first end portion 130, although those skilled in the art will recognize that the first tab 134 may define an arc that extends more or less than approximately 90 degrees around the outer perimeter of the first end portion 130. A tool-engageable section such as a slot 136 is inscribed in the first end portion 130, defining an actuating section. The slot 136 is sized to allow a tool (not shown), such as a flat head screwdriver or a side of a coin, to be inserted into the slot 136 to rotate the cylinder 124 within the valve body 121.

It may be seen in FIG. 2 (as well as in FIGS. 3 to 6) that the actuating sections of the first and second ends 130,132 of cylinder 124 extend beyond the lateral ends of the valve body 121 containing the cylinder-receiving valve passage 125, just sufficiently to be grasped by a tool or by fingertips of the practitioner or technician for rotation thereof, thereby reducing its exposure and thus minimize snagging with respect to foreign objects such as the patient's clothing, linens, wires and other tubing. As seen in FIG. 5, the cylinder 124 further includes a pair of grooves 137 that extend around a circumference of the cylinder 124 on either side of the opening 128. An O-ring 138 is disposed within each groove 137. The O-rings 138 seal any space between the exterior of the cylinder 124 and the interior of the body 121, preventing blood or other fluids from leaking out of the valve body 121. The O-rings 138 also act as a frictional stop between the cylinder 124 and the valve body 121 so that the cylinder 124 does not rotate freely within the valve body 121 absent an external rotational force to rotate the cylinder 124 relative to the valve body 121. Preferably, the cylinder 124 is formed from cylinder parts 124a, 124b that are bonded together after the O-rings 138 are inserted into their respective grooves 137. The cylinder parts 124a,124b may be bonded together by an adhesive, ultrasonic welding, or other suitable method known to those skilled in the art.

The body 110 may be formed by body parts 110a, 110b that are formed separately and bonded together during manufacture of the luer 100. The body 100 may be separated along the plane formed by section line 3-3 in FIG. 1. During manufacture, before joining the body parts 110a, 110b together, the cylinder 124 is inserted between the body parts 110a, 110b. After the cylinder 124 is inserted between the body parts 110a, 110b, the body parts 110a, 110b are connected together, such as by adhesive, ultrasonic bonding, or other suitable method known to those skilled in the art. In FIG. 2, it is shown that the cylinder 124 is of one piece, with the actuating sections 130, 132 being integrally formed therewith.

Figure 6:
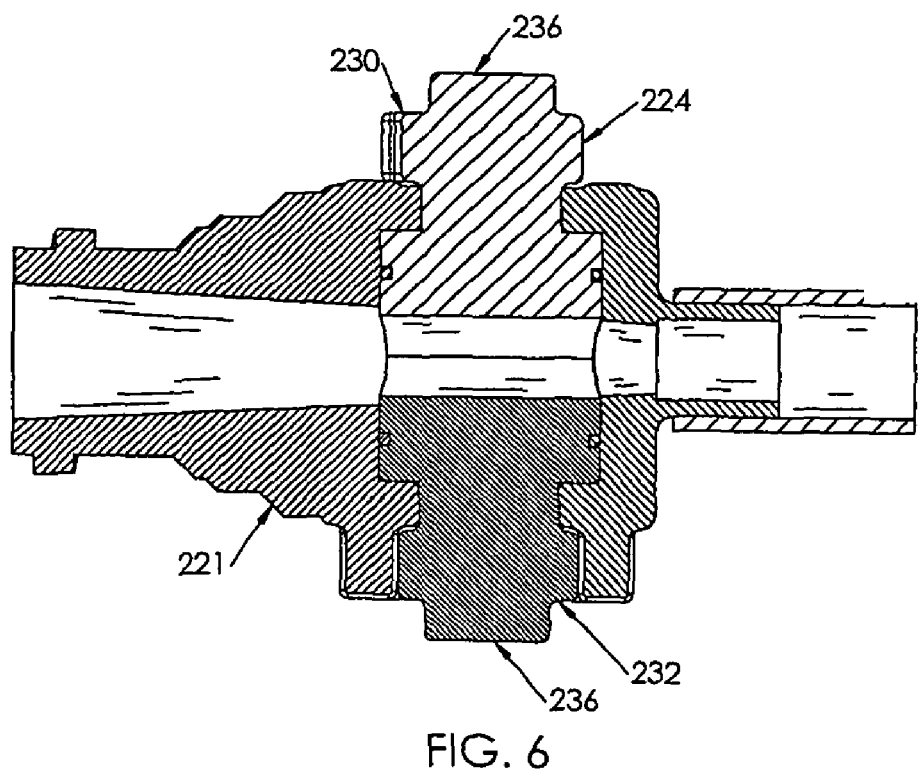
FIG. 6 is a longitudinal sectional view of the sealing luer according to a second embodiment of the present invention.

In an alternative embodiment of a cylinder 224, shown in FIG. 6, in lieu of the slot 136, a manually-engageable protrusion 236 may extend from the first end 230, to define an actuating section. The protrusion 236 is sized to allow a user to grasp the handle 236 to rotate the cylinder 224 within a valve body 221 without the need to use a tool. A second protrusion 236 may optionally extend from a second end 232 of the cylinder 224.

Figure 7:
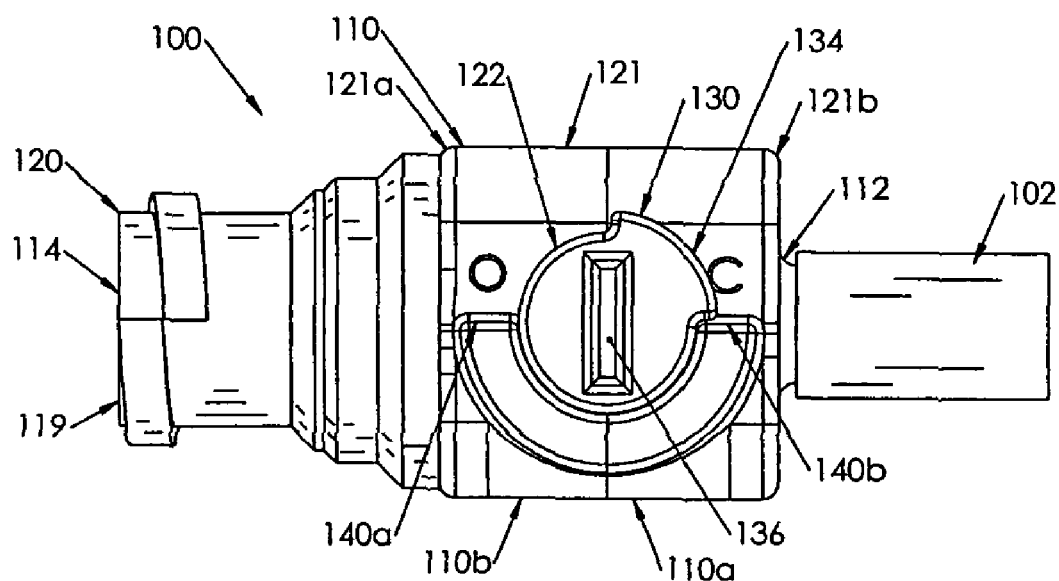
FIG. 7 is a side elevational view of the sealing luer according to the first embodiment of the present invention, with a sealing valve in the closed position.

Referring back to FIGS. 1 and 4, the valve body 121 proximate to the first end portion 130 of the cylinder 124 includes a stop 140 that extends preferably approximately 180 degrees around the exterior of the valve body 121. The stop 140 serves to engage the first tab 134 to stop rotation of the cylinder 124 within the body 121. As shown in FIG. 1, the first tab 134 is engaged with a first end portion 140a of the stop 140, and, as seen in the sectional view of FIG. 2, the opening 128 is aligned with the longitudinal passage 116, allowing fluid flow through the sealing luer 100. Rotation of the cylinder 124 in a clockwise direction as viewed in FIG. 1 rotates the first tab 134 toward a second end portion 140b of the stop 140, as shown in FIG. 7, rotating the opening 128 out of alignment with the longitudinal passage 116, and securing fluid flow through the sealing luer 100. Those skilled in the art will recognize that rotating the cylinder 124 partially between engagement with the first and second end portions 140a, 140b of the stop 140 will allow between no fluid flow and maximum fluid flow through the sealing luer 100, depending upon the degree of rotation of the cylinder 124 within the body 121.

While the stop 140 preferably extends approximately 180 degrees around the valve body 121 and the first tab 134 extends approximately 90 degrees around the first end portion 130 of the cylinder 124, those skilled in the art will recognize that the stop 140 may extend more or less than 180 degrees and that the first tab 134 may extend more or less than 90 degrees, so long as a difference between the arcuate lengths of the stop 140 and the first tab 134 is approximately 90 degrees.

Optionally, as seen in FIGS. 1 and 7, indicia may be printed on the body 121 to indicate the status of the valve 122 within the body 121. A first indicia, such as the letter "O" may be printed proximate to the first end portion 140a of the stop 140 to indicate that, when the first tab 134 is engaged with the first end portion 140a of the first stop 140, the valve 122 is open. Similarly, a second indicia, such as the letter "C" may be printed proximate to the second end portion 140b of the stop 140 to indicate that, when the first tab 134 is engaged with the second end portion 140b of the stop 140, the valve 122 is closed.

Also optionally, as seen in FIGS. 2 and 5, a second tab 142 may be disposed on the second end portion 132 of the cylinder 124 and a second stop 144 may be disposed around the valve body 121 proximate to the second end portion 132 of the cylinder 124. The second tab 142 engages the second stop 144 in the same manner as described above with respect to the first tab 134 and the first stop 140. Corresponding indicia may also be printed on the body 121 proximate to the second end portion 132 of the cylinder 124 to indicate the status of the valve 122 as described above. A slot 136 may be disposed within the second end portion 132 to enable a user to insert the tool to rotate the cylinder 124 with respect to the valve body 121.

Operation of the sealing luer 100 is as follows. With the proximal end 114 of the luer 100 connected to an external device, such as a hemodialysis machine, an infusion device, or other device (not shown), the external device is turned off after use according to standard operating procedures. At this time, the valve 122 is open, with the opening 128 and the longitudinal channel 116 being aligned with each other, permitting fluid communication between the proximal end 114 and the distal end 112 of the luer 100. Prior to disconnecting the luer 100 from the external device, a tool (not shown) is inserted into the slot 136 and the cylinder 124 is rotated within the valve body 121 approximately 90 degrees to close the valve 122, with the opening 128 being rotated to a position approximately perpendicular to the longitudinal channel 116, obstructing fluid communication between the proximal end 114 and the distal end 112 of the luer 100. The luer 100 may now be disconnected from the external device without the risk of blood flowing out of the catheter 102 from the proximal end 114 of the luer 100.

After disconnecting the external device, a syringe (not shown) containing a locking solution may be connected to the luer fitting 119 in order to fill the catheter 102 with the locking solution between dialysis treatments. The tool is again inserted into the slot 136, and the cylinder 124 is rotated to reopen the valve 122. The syringe is depressed, dispensing the locking solution through the sealing luer 100 and into the catheter 102. The valve 122 is again closed as described above, and the syringe is removed from the luer fitting 119. A cap (not shown) is screwed over the connection 120 to provide a redundant closure to prevent the locking solution and blood from discharging from the sealing luer 100. The luer 100 is now sealed with the redundant protection of the cap over the connection 120 and with the valve 122 being closed.

To open the luer 100, the cap is first unthreaded from the connection 120. A syringe (not shown) is connected to the luer fitting 119. The tool is inserted into the slot 136 and rotated approximately 90 degrees in a direction, such a counter-clockwise direction, to open the valve 122. The syringe is operated to draw any locking solution from the catheter 102 into the syringe. The valve 122 is then rotated approximately 90 degrees in an opposing direction, such as a clockwise direction, to close the valve 122 and to allow the syringe to be removed without allowing blood in the catheter 102 to drain from the proximal end 114 of the luer 100. The syringe is removed and the luer fitting 119 is connected to the external device for use. The valve 122 is then rotated approximately 90 degrees in a direction, such a counter-clockwise direction, to open the valve 122, so that the external device is in fluid communication with the catheter 102.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A connector for being secured to a catheter that extends into a venous opening of a patient, comprising:
a body having a proximal end, a distal end adapted to be secured to a proximal end of a catheter lumen, and a single axially extending passage extending therethrough between the proximal end and the distal end, fluidly connecting the proximal end and the distal end, wherein the proximal end includes a fitting for releasably connecting the connector to an external device, the body further having a valve body containing a cylinder-receiving passage extending transversely with respect to the axially extending passage to first and second valve body ends;
a cylinder rotatably disposed within the cylinder-receiving passage of the valve body and being rotatable between a first position and a second position, wherein the cylinder includes an opening extending generally diametrically therethrough, and further includes first and second cylinder ends at least one of which includes a manually grippable actuating section integrally formed with the at least one cylinder end, and each said at least one actuating section extends beyond the lateral ends of the valve body to be engaged for rotation by the practitioner or technician and is free of projections extending orthogonally therefrom beyond the valve body, thereby reducing its exposure and minimizing snagging thereof by foreign objects,
wherein the valve body further comprises a stop extending from the valve body a selected distance parallel to the cylinder-receiving passage, and the at least one actuating section comprises a tab engageable with the stop to limit rotation of the cylinder, the tab and actuating section co-extending outwardly from the valve body a distance equal to the selected distance such that the stop, the tab and the actuating section together reduce their exposure and minimize snagging by foreign objects; and at least one seal is disposed about the cylinder and within the passage on each side of the opening, wherein when the cylinder is in the first position, the proximal end of the body is in fluid communication with the distal end of the body and wherein, when the cylinder is in the second position, the proximal end of the body is not in fluid communication with the distal end of the body.

2. The connector according to claim 1, wherein the body comprises a first stop portion disposed along an outer diameter of the at least one actuating section and a second stop portion disposed a predetermined arcuate distance from the first stop, and wherein the tab is movably disposed between the first stop portion and the second stop portion so that, when the tab is movably disposed proximate to the first stop portion, the cylinder is in one of an open position and a closed position, and when the tab is movably disposed proximate to the second stop portion, the cylinder is in the other of the open position and the closed position.

3. The connector according to claim 2, wherein the body further comprises first indicia disposed proximate to the first stop portion and second indicia disposed proximate to the second stop portion, wherein the first indicia indicates one of an open and closed position, and the second indicia indicates the other of the open and closed position.

4. The connector according to claim 1, wherein the fitting for releasably connecting the connector comprises an externally threaded connector.

5. The connector according to claim 1, wherein the cylinder further comprises a tool-engageable slot defined into each of the first and second ends of the cylinder to allow engagement by a tool to operate the cylinder between the open position and the closed position.

6. The connector according to claim 1, wherein each of the first and second cylinder ends include a manually grippable and rotatable actuating section.

7. The connector according to claim 1, wherein the body comprises initially separate first and second portions associated respectively with the distal and proximal ends, and the first and second portions are affixed to each other at an interface that defines a pair of semicylindrical surfaces that cooperate to define the cylinder-receiving passage, and the cylinder is placed in the interface during assembly to be contained within the cylinder-receiving passage upon full assembly, and wherein the cylinder comprises a reduced diameter portion adjacent each cylinder end within which complementarily dimensioned valve body sections of the first and second portions are received upon assembly thereby retaining the cylinder within the cylinder-receiving passage upon assembly while permitting cylinder rotation.

8. A connector for being secured to a catheter that extends into a venous opening of a patient, comprising:

a body having a proximal end, a distal end adapted to be secured to a proximal end of a catheter lumen, and a single axially extending passage extending therethrough between the proximal end and the distal end, fluidly connecting the proximal end and the distal end, wherein the proximal end includes a fitting for releasably connecting the connector to an external device, the body further having a valve body containing a cylinder-receiving passage extending transversely with respect to the axially extending passage to first and second valve body ends; and a cylinder rotatably disposed within the cylinder-receiving passage of the valve body and being rotatable between a first position and a second position, wherein the cylinder includes an opening extending generally diametrically therethrough, and further includes first and second cylinder ends at least one of which includes a manually grippable actuating section, and each said at least one actuating section extends beyond the lateral ends of the valve body to be engaged for rotation by the practitioner or technician and is free of projections extending orthogonally therefrom beyond the valve body, thereby reducing its exposure and minimizing snagging thereof by foreign objects, wherein the body comprises initially separate first and second portions associated respectively with the distal and proximal ends, and the first and second portions are affixed to each other at an interface that defines a pair of semicylindrical surfaces that cooperate to define the cylinder-receiving passage, and the cylinder is placed in the interface during assembly to be contained within the cylinder-receiving passage upon full assembly, wherein the cylinder comprises a reduced diameter portion adjacent each cylinder end within which complementarily dimensioned valve body sections of the first and second portions are received upon assembly thereby retaining the cylinder within the cylinder-receiving passage upon assembly while permitting cylinder rotation, and wherein when the cylinder is in the first position, the proximal end of the body is in fluid communication with the distal end of the body and wherein, when the cylinder is in the second position, the proximal end of the body is not in fluid communication with the distal end of the body.

9. The connector according to claim 8, wherein the cylinder further comprises a tool-engageable slot defined into each of the first and second ends of the cylinder to allow engagement by a tool to operate the cylinder between the open position and the closed position.

10. The connector according to claim 8, wherein each of the first and second cylinder ends include a manually grippable actuating section.

* * * * *